United States Patent [19]

Ross et al.

[11] 4,259,343

[45] Mar. 31, 1981

[54] OXAZOLE CARBAMATES, FORMULATIONS AND ASTHMA TREATMENT

[75] Inventors: William J. Ross, Lightwater; Alec Todd, Wokingham; John P. Verge, Henley-on-Thames, all of England

[73] Assignee: Lilly Industries Limited, London, England

[21] Appl. No.: 9,335

[22] Filed: Feb. 5, 1979

Related U.S. Application Data

[60] Division of Ser. No. 864,900, Dec. 27, 1977, Pat. No. 4,175,131, which is a continuation of Ser. No. 678,015, Apr. 19, 1976, abandoned.

[30] Foreign Application Priority Data

May 2, 1975 [GB] United Kingdom ............... 18320/75

[51] Int. Cl.³ ............................................. A61K 31/42
[52] U.S. Cl. .................................................. 424/272
[58] Field of Search ............... 548/233, 234; 542/414; 424/272

[56] References Cited

U.S. PATENT DOCUMENTS

| | | | |
|---|---|---|---|
| 3,290,326 | 12/1966 | Hoffer | 260/307 R |
| 3,682,945 | 8/1972 | Engelhart | 260/307 R |
| 3,705,903 | 12/1972 | Crank | 260/307 R |
| 3,809,755 | 5/1974 | Crank | 424/272 |

OTHER PUBLICATIONS

C. Tanaka et al., Chem. Abstracts 58:3408C (1963), Synthesis of 5- or 2-oxazole carboxylic acids and aminooxazoles.

*Primary Examiner*—Donald G. Daus
*Assistant Examiner*—M. C. Eakin
*Attorney, Agent, or Firm*—Charles W. Ashbrook; Arthur R. Whale

[57] ABSTRACT

A class of novel 2-oxazolyl ureas and carbamates having anti-allergic activity are described together with methods of making such compounds and pharmaceutical compositions containing the active compounds of the invention.

10 Claims, No Drawings

OXAZOLE CARBAMATES, FORMULATIONS AND ASTHMA TREATMENT

This is a division of application Ser. No. 864,900, filed Dec. 27, 1977, now U.S. Pat. No. 4,175,131, issued Nov. 20, 1979 which was a continuation of Ser. No. 678,015, filed Apr. 19, 1976, now abandoned.

This invention relates to heterocyclic compounds, more particularly to certain novel oxazole derivatives which possess useful pharmacological activity and/or are useful as intermediates in preparing such active compounds. The invention also includes processes for preparing the compounds of the invention. Furthermore, the invention includes within its scope pharmaceutical compositions containing the pharmacologically active compounds and methods of treatment of animals, including humans, comprising administering thereto an effective dose of an active compound of the invention.

United Kingdom Patent Specification No. 1,327,042 describes and claims a class of oxazole ureas similar to those of the present invention which possess anti-inflammatory properties together with some activity in the central nervous system. However, this patent specification is totally silent concerning anti-allergic activity.

The Applicants have now unexpectedly discovered that a novel series of oxazole derivatives produced by modification of the structures disclosed in the above-mentioned specification possess significant activity against allergic conditions, specifically against immediate hypersensitivity diseases.

Accordingly the present invention provides a novel oxazole derivative of formula (I):

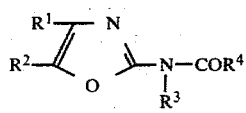

(I)

wherein $R^1$ and $R^2$ are independently hydrogen, $C_{1-6}$ alkyl, $C_{1-4}$ hydroxyalkyl, $C_{3-8}$ cycloalkyl, $C_{3-6}$ acyloxyalkyl or an optionally substituted phenyl group; $R^3$ is hydrogen, $C_{1-6}$ alkyl, $C_{2-6}$ alkenyl, $C_{3-6}$ alkoxyalkyl, $C_{3-8}$ cycloalkyl, $C_{3-8}$ cycloalkyl-$C_{1-4}$ alkyl, optionally substituted phenyl-$C_{1-4}$ alkyl or optionally substituted phenyl-$C_{2-4}$ alkenyl; and $R^4$ represents the group $NHR^5$ or $OR^5$ where $R^5$ is $C_{1-6}$ alkyl, $C_{3-8}$ cycloalkyl, $C_{2-4}$ alkenyl, optionally substituted phenyl, $C_{1-6}$ haloalkyl, or aralkyl containing from 7 to 10 carbon atoms; provided that, in the case where $R^4$ represents $NHR^5$, $R^3$ cannot be hydrogen when all of $R^1$, $R^2$ and $R^5$ are selected from hydrogen, $C_{1-6}$ alkyl and optionally substituted phenyl.

The term "$C_{1-6}$ alkyl" as used herein means a straight or branched chain alkyl group containing from 1 to 6 carbon atoms such as methyl, ethyl, isopropyl, n-butyl, s-butyl, isobutyl, t-butyl, n-amyl, s-amyl, n-hexyl, 2-ethylbutyl and 4-methylamyl. Similarly, the term "$C_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl.

"$C_{1-4}$ hydroxyalkyl" and "$C_{3-6}$ acyloxyalkyl" means the aforementioned $C_{1-4}$ alkyl groups substituted with an hydroxy group and acyloxy group respectively. "$C_{3-6}$ alkoxyalkyl" and "$C_{1-6}$ haloalkyl" mean the aforementioned $C_{1-6}$ alkyl groups substituted with an alkoxy group or one or more halogen atoms, such as methoxyethyl, ethoxyethyl, ethoxybutyl, dibromomethyl, trifluoromethyl, 1-chloroethyl, 1,1-dichloroethyl, 1-iodobutyl and pentafluoroethyl. The alkoxyalkyl group must not contain an alkoxy group attached to the carbon atom directly adjacent the nitrogen atom.

"$C_{3-8}$ cycloalkyl" means a saturated ring having from 3 to 8 carbon atoms in the ring such as cyclopropyl, cyclobutyl, cyclopentyl, and cyclooctyl. "$C_{3-8}$ cycloalkyl-$C_{1-4}$ alkyl" means the aforementioned saturated rings attached to the nitrogen atom via a $C_{1-4}$ alkylene bridge.

The term "optionally substituted phenyl" as used herein means a phenyl group unsubstituted or substituted by one or more groups which do not substantially alter the pharmacological activity of the compounds of formula (I) such as halogen, trifluoromethyl, methyl, methoxy, or nitro groups.

Preferred carbamates (i.e. compounds of formula (I) in which $R^4$ is $OR^5$) and preferred ureas (i.e. compounds of formula (I) in which $R^4$ is $NHR^5$) of the invention are those having one or more of the following features:

(A) $R^1$ is hydrogen;
(B) $R^1$ is $C_{1-4}$ alkyl;
(C) $R^1$ is methyl;
(D) $R^2$ is hydrogen;
(E) $R^2$ is $C_{1-4}$ alkyl;
(F) $R^2$ is methyl;
(G) $R^3$ is $C_{1-4}$ alkyl;
(H) $R^3$ is benzyl;
(I) $R^5$ is $C_{1-6}$ alkyl;
(J) $R^5$ is $C_{1-4}$ alkyl;
(K) $R^5$ is optionally substituted phenyl;
(L) $R^5$ is $C_{3-8}$ cycloalkyl; or
(M) $R^5$ is $C_{1-6}$ haloalkyl, such as trifluoromethyl.

The preferred ureas in accordance with the present invention have the formula

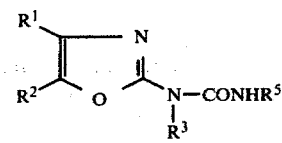

wherein $R^1$ and $R^2$ are independently hydrogen, $C_{1-4}$ alkyl, $C_{1-2}$ hydroxyalkyl, $C_{3-4}$ acyloxyalkyl or phenyl;

$R^3$ is hydrogen, $C_{1-6}$ alkyl, $C_{5-7}$ cycloalkyl, $C_{5-7}$ cycloalkyl-$C_{1-3}$ alkyl, phenyl-$C_{1-3}$ alkyl or phenyl-$C_{2-3}$ alkenyl; and $R^5$ is $C_{1-6}$ alkyl, $C_{5-7}$cycloalkyl, $C_{2-4}$ alkenyl, phenyl optionally substituted by one halogen radical or $C_{1-4}$ haloalkyl.

The most preferred ureas are those in which $R^1$ is methyl, $R^2$ is hydrogen, $R^3$ is n-butyl and $R^5$ is ethyl, allyl, phenyl, or —$CH_2$—$CH_2$—Cl.

The preferred carbamates in accordance with the present invention have the formula

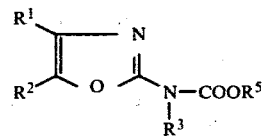

wherein $R^1$ and $R^2$ are independently hydrogen, $C_{1-4}$ alkyl, $C_{1-3}$ hydroxyalkyl or $C_{5-7}$ cycloalkyl;

$R^3$ is $C_{1-4}$ alkyl, $C_{2-4}$ alkenyl, $C_{3-4}$ alkoxyalkyl or $C_{5-7}$ cycloalkyl; and $R^5$ is $C_{1-4}$ alkyl, $C_{5-7}$ cycloalkyl, $C_{2-4}$ alkenyl or phenyl-$C_{1-3}$ alkyl.

The most preferred carbamates are those in which $R^1$ is methyl, $R^2$ is hydrogen, $R^3$ is n-butyl and $R^5$ is $C_{2-4}$ alkyl.

The present invention also provides a method of preparing a compound of formula (I) which comprises reacting an oxazole of formula:

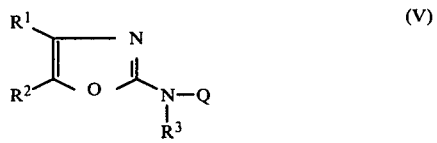 (V)

with a compound of formula $R^{5'}Z$, (a) wherein (i) Q is hydrogen, $R^{5'}$ is $R^5$ or hydrogen and Z is —NCO; or (ii) Q is COCl, $R^{5'}$ is $R^5$ and Z is $NH_2$;

so as to produce a compound of formula (I) in which $R^4$ is —$NHR^{5'}$, followed, when $R^{5'}$ is hydrogen, by alkylation of one of the primary amino hydrogen atoms in the —$NHR^{5'}$ moiety with an alkylating agent of formula $R^5X$, where X is a reactive atom or group, such as a halogen atom or a sulphonate group;

(b) wherein Q is hydrogen, Z is $LCO_2$— where L is a good leaving group, preferably chlorine, and $R^{5'}$ is $R^5$, so as to produce a compound of formula (I) in which $R^4$ is $OR^5$, followed, if desired, when $R^3$ is hydrogen, by alkylation with an alkylating agent of formula $R^3X$, $R^3$ being $C_{1-6}$ alkyl, $C_{2-6}$ alkenyl, $C_{3-6}$ alkoxyalkyl, optionally substituted phenyl $C_{1-4}$ alkyl, or optionally substituted phenyl-$C_{2-4}$ alkenyl, so as to form a compound of formula (I) where $R^4$ is $OR^5$ and $R^3$ is not hydrogen.

The preferred method of preparation of ureas of formula (I) involves the reaction of a secondary amine of formula (V) in which Q is hydrogen and $R^3$ is other than hydrogen, with an isocyanate of formula $R^5NCO$, i.e. where Z is —NCO. This reaction can be illustrated by the following reaction scheme:

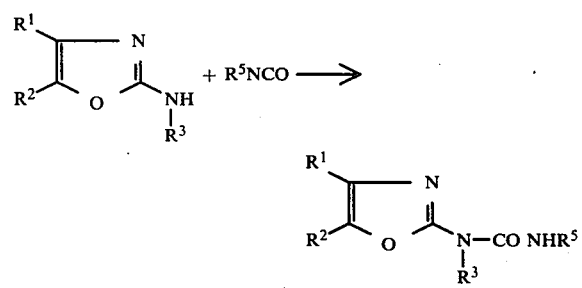

The reaction can be carried out in any suitable anhydrous inert solvent, such as, for example, benzene or toluene. Similar reaction conditions to those described in U.K. Patent Specification No. 1,327,042 may be utilised.

In a modification of the above isocyanate method the reactive entity $R^5NCO$ can be replaced by isocyanic acid (HNCO) conveniently prepared in situ from an alkali metal isocyanate, for example, potassium isocyanate, and a carboxylic acid such as acetic acid. The product of the reaction is the oxazole shown below:

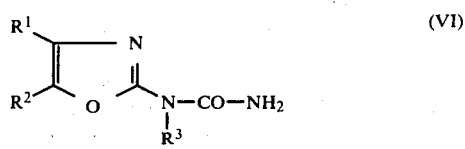 (VI)

This compound is then alkylated with an alkylating agent to form a urea of the invention. The alkylation is best carried out in the presence of an acid acceptor such as a base. It should be noted that the term "alkylation" is used herein in a broad sense to indicate the addition of moieties such as alkenyl, $C_{1-6}$ haloalkyl or $C_{7-10}$ aralkyl to the oxazole molecule, as well as, of course, the $C_{1-6}$ alkyl and $C_{3-8}$ cycloalkyl moeities. One method of alkylating a compound of formula (VI) comprises forming the sodium salt thereof with NaH in dimethylformamide and then treating the salt with an alkyl halide or sulphonate. In those cases where $R^3$ is hydrogen, it has been found that selective alkylation occurs initially at one of the primary amino hydrogen atoms.

The intermediate of formula (VI) is novel as is its conversion to a compound of formula (I) and accordingly both of these features are provided in further aspects of the invention.

When a carbamoyl chloride of formula (V), i.e. a compound of formula (V) where Q is COCl, is reacted with an amine of formula $R^5NH_2$, the reaction can be accomplished by the use of excess amine and/or in the presence of an acid acceptor, such as triethylamine, which will not react with the carbamoyl chloride.

When a compound of formula (V) in which Q is hydrogen is reacted with a compound of formula $LCO_2R^5$, the product of the reaction is a carbamate of formula (I). The reaction proceeds via the intermediate of formula (II):

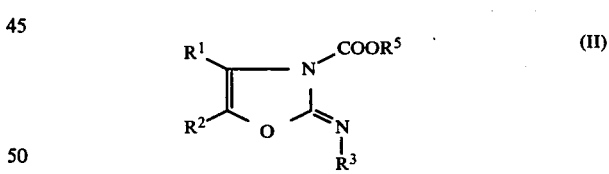 (II)

where $R^1$, $R^2$, $R^3$ and $R^5$ are as defined above. The above compound of formula (II) is thermally unstable and readily rearranges to form a compound of formula (I). However, although unstable this compound can, if desired, be isolated. As indicated above, it is highly preferred that the leaving group L be a chlorine atom. In such a case the reaction can be schematically illustrated as shown below:

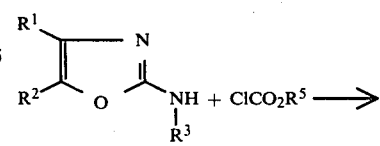

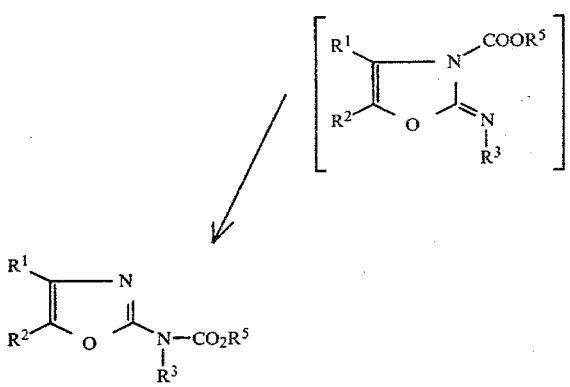

The reaction can be carried out in an inert solvent such as dry ether and in the presence of a suitable proton acceptor such as triethylamine.

Final products of the above reaction in which $R^3$ is hydrogen may be converted to the corresponding alkylated derivatives by treatment with suitable alkylating agents such as alkyl iodides. It is considered that it is unnecessary to give specific examples of suitable reagents or reaction conditions, these being well-known to those skilled in the art.

Compounds of formula I have been shown to be useful in the prophylactic and therapeutic treatment of immediate hypersensitivity diseases including asthma and in the alleviation of status asthmaticus. The compounds have low toxicity.

The compounds or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula I. Dosages of from 0.5 to 300 mg/kg per day, preferably 0.5 to 20 mg/kg of active ingredient may be administered although it will, of course, readily be understood that the amount of the compound or compounds of formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidine, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The invention will now be further illustrated with reference to the following Examples.

EXAMPLE 1

1-Butyl-3-ethyl-1-(4-methyl-2-oxazolyl)urea

A solution of 2-butylamino-4-methyloxazole (15.0 g, 0.0972 mol) and ethyl isocyanate (7.6 g, 0.107 mol) in dry benzene was heated under reflux for 2 hours and then evaporated to dryness. The residual oil was dissolved in ether and the solution was washed with 2 N HCl, dried and evaporated. The residue was distilled under vacuum b.p. 128° C./1.0 mm. IR 3275, 1696, 1590 cm$^{-1}$.

Analysis: C: 58.37; H: 8.30; N: 18.89; O: 14.44. $C_{11}H_{19}N_3O_2$ requires C: 58.64; H: 8.50; N: 18.64; O: 14.20%.

EXAMPLE 2

1,3-Dibutyl-1-(4-methyl-2-oxazolyl)urea(b.p. 128° C./0.2 mm) was prepared using a similar method to that of Example 1.

EXAMPLE 3

1-Butyl-3-hexyl-1-(4-methyl-2-oxazolyl)urea

A solution of 2-butylamino-4-methyloxazole (10.0 g, 0.065 mol) and hexyl isocyanate (8.25 g, 0.065 mol) in dry benzene was heated under reflux for 3 hours. The solution was evaporated and the residual oil dissolved in ether, washed with dilute HCl, dried and re-evaporated. The residue was dissolved in petroleum spirit (40°–60°

C.) carbon treated and re-evaporated under vacuum to give the pure product as a pale oil.

Analysis: C: 63.77; H: 9.84; N: 14.49; O: 11.55. $C_{15}H_{27}N_3O_2$ requires C: 64.02; H: 9.67; N: 14.93; O: 11.37%.

EXAMPLES 4 to 21

The following ureas were prepared by similar methods to those described in Examples 1 to 3. In some cases the products solidified and, if necessary, were recrystallised from the solvent systems indicated in the following Table.

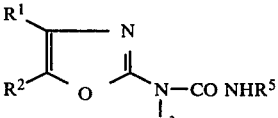

| Ex. No. | $R^3$ | $R^1$ | $R^2$ | $R^5$ | m.p. °C. (solvent system) |
|---|---|---|---|---|---|
| 4 | n-Bu | Me | H | —CMe₃ | 45–46 (EtOH—H₂O) |
| 5 | n-Bu | Me | H | cyclohexyl | 30–35 |
| 6 | n-Bu | Me | H | —CH₂CH₂Cl | |
| 7 | n-Bu | Me | H | Ph | 41–42 (EtOH—H₂O) |
| 8 | n-Bu | Me | H | o-ClPh | 48–49 (EtOH—H₂O) |
| 9 | n-Bu | Me | H | Cl-Ph | 91–92 (EtOH—H₂O) |
| 10 | n-Bu | Me | H | Ph-Cl | 88 (EtOAc) |
| 11 | nC₅H₁₁ | Me | H | Et | |
| 12 | —CH₂Ph | Me | H | Et | 56–57 |
| 13 | —CH₂Ph | Me | H | n-Bu | |
| 14 | n-Bu | Me | Me | Ph | 79–80 (EtOH—H₂O) |
| 15 | n-Bu | Me | Me | Cl-Ph | 66–68 (CHCl₃) |
| 16 | —CH₂C₆H₁₁ | i-Pr | H | n-Bu | |
| 17 | n-Bu | Me | hydroxymethyl | i-Pr | |
| 18 | cyclohexyl | Me | H | Et | |
| 19 | Me | Ph | H | —CMe₃ | |
| 20 | Me | H | acetyloxymethyl | Et | |
| 21 | styryl | n-Bu | Me | —CF₃ | |

EXAMPLE 22

1-Allyl-3-butyl-3-(4-methyl-2-oxazolyl)urea

A solution of 2-butylamino-4-methyloxazole (12.0 g, 0.078 mol) and allyl isocyanate (6.46 g, 0.078 mol) in dry benzene was heated under reflux for 4 hours, and worked up as described in Example 3. The product was further purified by chromatography on a silica-gel column, eluting with a 1:1 mixture of benzene and ethyl acetate.

Analysis: C: 60.47; H: 7.80; N: 17.42; O: 13.73. $C_{12}H_{19}N_3O_2$ requires: C: 60.74; H: 8.07; N: 17.70; O: 13.48%.

EXAMPLE 23

Ethyl N-butyl-N-(4-methyl-2-oxazolyl)-carbamate

Ethyl chloroformate (10.5 ml, 0.11 mol) was added dropwise over 20 minutes to a stirred solution of 2-butylamino-4-methyl oxazole (15.4 g, 0.10 mol) and triethylamine (15.3 ml, 0.11 mol) in dry ether (100 ml) cooling to 5°–10° C. The mixture was stirred for a further 2 hours at ambient temperature, the white solid was filtered off and the filtrate evaporated under vacuum to a pale oil (22.4 g) NMR (CCl₄) 6.3 δ (oxazole 5-H). This 3-acylated compound was dissolved in xylene and the solution was heated under reflux for 2 hours, cooled, washed with dilute HCl, saturated NaCl solution, dilute Na₂CO₃ and NaCl solution again, dried and evaporated. The residue was distilled under vacuum, b.p. 85°–90° C./0.6 mm NMR (CCl₄) 7.12 δ (oxazole 5-H).

Analysis: C: 58.58; H: 7.90; N: 12.12. $C_{11}H_{18}N_2O_3$ requires C: 58.39; H: 8.02; N: 12.38%.

EXAMPLES 24 TO 27

The following compounds were prepared by similar methods to that of Example 23:

| Ex. No. | $R^5$ | $R^2$ | b.p. °C./ pressure m.m. Hg |
|---|---|---|---|
| 24 | n-Bu | H | 98–102/0.3 mm |
| 25 | —CH₂CH Me₂ | H | 110–113/1.0 mm |
| 26 | —CH₂Ph | H | 138–140/0.2 mm |
| 27 | Et | Me | 100–102/1.2 mm |

EXAMPLE 28

Ethyl N-(4-methyl-2-oxazolyl)carbamate

Ethyl chloroformate (1.05 ml, 0.011 mol) was added dropwise to a stirred solution of 2-amino-4-methyloxazole (1.0 g, 0.010 mol) and triethylamine (1.5 ml, 0.011 mol) in dry ether (50 ml) at 5°–10° C. The mixture was stirred for 2 hours at 0°–5° C. then the white solid was filtered off and washed well with water to remove triethylamine hydrochloride. Residue (0.5 g) was recrystallised from chloroform-petroleum spirit, m.p. 126° C.

Analysis: C: 49.35; H: 6.16; N: 16.64. $C_7H_{10}N_2O_3$ requires C: 49.40; H: 5.92; N: 16.46%.

EXAMPLE 29

Alkylation of the product of Example 28 with sodium hydride-butyl iodide yielded ethyl N-butyl-N-(4-methyl-2-oxazolyl)carbamate.

EXAMPLES 30–35

The following further carbamates were prepared using modifications of the processes described in Examples 23, 28 and 29.

n-Butyl N-methyl-N-(4-n-butyl-2-oxazolyl)-carbamate.
Ethyl N-cyclohexyl-N-(4-methyl-2-oxazolyl)-carbamate.
Ethyl N-butyl-N-(4-hydroxymethyl-2-oxazolyl)-carbamate.
Cyclohexyl N-allyl-N-(4-methyl-2-oxazolyl)-carbamate.

Allyl N-methoxyethyl-N-(4-cyclohexyl-2-oxazolyl)-carbamate.
Benzyl N-methyl-N-(4-methyl-2-oxazolyl)-carbamate.

EXAMPLES 36 and 37

The following further ureas were prepared by similar procedures to those described in Examples 1 and 3.
1-cyclohexyl-3-(4-methyl-2-oxazolyl)urea m.p. 151°–2° C.
1-cyclohexyl-3-(4,5-dimethyl-2-oxazolyl)urea m.p. 155°–7° C.

The above structure assignments were confirmed by spectral data.

The following Examples illustrate pharmaceutical formulations containing the active compound 1-butyl-3-ethyl-1-(4-methyl-2-oxazolyl)urea.

EXAMPLE 38

Soft gelatin capsules were prepared using the following ingredients:

|  | Quantity (mg/capsule) |
|---|---|
| Active compound | 20 |
| Butylated hydroxyanisole B.P. | 0.03 |
| Fractionated Coconut Oil B.P.C. | 70 |
|  | 90.03 |

The above ingredients were mixed and filled into soft gelatin capsules, the main shell components of which were gelatin and glycerine.

EXAMPLE 39

The procedure of Example 38 was repeated except that an identical quantity of propyl gallate was used in place of the butylated hydroxyanisole as antioxidant.

EXAMPLE 40

Hard gelatin capsules were prepared using the following ingredients:

|  | Quantity (mg/capsule) |
|---|---|
| Active compound | 27 |
| Silicon dioxide (fumed) | 27 |
| Lactose | 54 |
| Butylated hydroxyanisole B.P. | 0.03 |

The butylated hydroxyanisole was dissolved in the active ingredient and the solution so formed adsorbed onto the silicone dioxide (fumed). The lactose was then added and the whole mixed. Finally, the mixture was filled into hard gelatin capsules.

Alternatively, the solution of butylated hydroxyanisole and active compound can be diluted with an inert solvent, the solution slurried onto the silicone dioxide (fumed) and the inert solvent evaporated off. The lactose is then mixed in and the mixture filled into the hard gelatin capsules.

EXAMPLE 41

An injectible solution was prepared containing the following components:

| Active ingredient | 20 | mg. |
|---|---|---|
| Cremophor EL | 20 | mg. |
| Ethanol | 20 | mg. |
| Water | 20 | mg. |

| -continued | |
|---|---|
| Butylated hydroxyanisole B.P. | 0.02 mg. |

The butylated hydroxyanisole was dissolved in the active ingredient and ethanol, the water and Cremophor EL added and the solution sterilised by filtration through a bacteria proof filter into sterile containers.

EXAMPLE 42

Suppositories containing 25 and 50 mg. of the compound were prepared as follows:

| Active compound | 2.5 g. |
|---|---|
| Henkel base | 97.5 g. |

The active compound was mixed with the Henkel base which had been previously melted using the minimum amount of heat possible. The mixture was then poured into suppository moulds of a nominal capacity of 1 g. or 2 g. as desired, to produce suppositories each containing 25 mg. or 50 mg. of the active compound.

EXAMPLE 43

An aerosol was prepared containing the following ingredients:

|  | Quantity per ml. |
|---|---|
| Active compound | 15.00 mg. |
| Propylene glycol | 15.00 mg. |
| Dichlorotetrafluoroethane (Propellant 114) | 600.00 mg. |
| Dichlorodifluoromethane (Propellant 12) | 850.00 mg. |

The active compound was mixed with the propylene glycol and the mix added to the propellant 114, the mixture cooled to −15° to −20° C. and transferred to a filling device. At the same time a mixture of propellants 114 and 12, previously cooled to −15° to −20° C. was fed into a second filling device. A metered amount of propellant from the second filling device was introduced into a stainless steel container, followed by the required amount of material from the first filling device. The valve units were then fitted and sealed to the container. These valve units may be equipped with metering device so that approximately 0.15 mg. of the active compound is released by a single actuation of the valve.

EXAMPLE 44

Tablets were prepared using the following components:

| Active compound | 20.00 | mg. |
|---|---|---|
| Microcrystalline Cellulose | 240.00 | mg. |
| Sodium Carboxymethyl Starch | 30.00 | mg. |
| Magnesium Stearate | 4.00 | mg. |
| Butylated Hydroxyanisole B.P. | 0.002 | mg. |

The hydroxyanisole was dissolved in the active compound, the solution adsorbed onto the microcrystalline cellulose. This was mixed with the sodium carboxymethylcellulose and then the magnesium stearate was mixed in. Finally, the mixture was compressed to form tablets.

In the foregoing Examples 38 to 44, the liquid active compound used may, in accordance with the invention, be replaced wholly or in part by other liquid active compounds of formula I. If the active compound is a solid, appropriate modification will of course have to be made.

We claim:

1. A method of treating an animal suffering from an allergic condition which comprises administering to an afflicted animal a chemotherapeutically effective amount of an oxazole of the formula

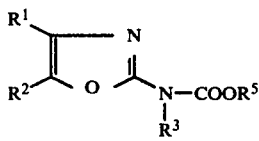

wherein:
$R^1$ and $R^2$ are independently hydrogen, $C_{1-6}$ alkyl, $C_{1-4}$ hydroxyalkyl, $C_{3-8}$ cycloalkyl, $C_{3-6}$ alkanoyloxyalkyl, phenyl, halophenyl, trifluoromethylphenyl, methylphenyl, methoxyphenyl, or nitrophenyl;
$R^3$ is hydrogen, $C_{1-6}$ alkyl, $C_{2-6}$ alkenyl, $C_{3-6}$ alkoxyalkyl, $C_{3-8}$ cycloalkyl, $C_{3-8}$ cycloalkyl-$C_{1-4}$ alkyl, phenyl-$C_{1-4}$ alkyl, halophenyl-$C_{1-4}$ alkyl, trifluoromethylphenyl-$C_{1-4}$ alkyl, methylphenyl-$C_{1-4}$ alkyl, methoxyphenyl-$C_{1-4}$ alkyl, nitrophenyl-$C_{1-4}$ alkyl, phenyl-$C_{2-4}$ alkenyl, halophenyl-$C_{2-4}$ alkenyl, trifluoromethylphenyl-$C_{2-4}$ alkenyl, methylphenyl-$C_{2-4}$ alkenyl, methoxyphenyl-$C_{2-4}$ alkenyl, or nitrophenyl-$C_{2-4}$ alkenyl; and
$R^5$ is $C_{1-6}$ alkyl, $C_{3-8}$ cycloalkyl, $C_{2-4}$ alkenyl, phenyl, halophenyl, trifluoromethylphenyl, methylphenyl, methoxyphenyl, nitrophenyl, or $C_{1-6}$ haloalkyl.

2. The method according to claim 1 employing a compound wherein $R^1$ and $R^2$ are independently hydrogen, $C_{1-4}$ alkyl, $C_{1-3}$ hydroxyalkyl, or $C_{5-7}$ cycloalkyl; $R^3$ is $C_{1-4}$ alkyl, $C_{2-4}$ alkenyl, $C_{3-4}$ alkoxyalkyl, or $C_{5-7}$ cycloalkyl; and $R^5$ is $C_{1-4}$ alkyl, $C_{5-7}$ cycloalkyl, or $C_{2-4}$ alkenyl.

3. The method according to claim 2 employing a compound wherein $R^1$ is methyl.

4. The method according to claim 3 employing a compound wherein $R^2$ is hydrogen.

5. The method according to claim 4 employing a compound wherein $R^3$ is n-butyl.

6. The method according to claim 5 employing a compound wherein $R^5$ is $C_{2-4}$ alkyl.

7. The method according to claim 6 employing a compound wherein $R^5$ is ethyl.

8. The method according to claim 6 employing a compound wherein $R^5$ is n-propyl.

9. The method according to claim 6 employing a compound wherein $R^5$ is n-butyl.

10. The method according to claim 1 wherein the allergic condition treated is asthma.